US011639441B2

(12) United States Patent
Whiteman et al.

(10) Patent No.: US 11,639,441 B2
(45) Date of Patent: May 2, 2023

(54) INORGANIC PARTICULATE MATERIAL SUITABLE FOR USE IN POLYMERIC FILMS

(71) Applicant: ImerTech SAS, Paris (FR)

(72) Inventors: David James Whiteman, Par Cornwall (GB); Craig Deporter, Lupsingen (CH); Sabine Gomila, Villers (FR)

(73) Assignee: ImerTech SAS, Paris (FR)

( * ) Notice: Subject to any disclaimer, the term of this patent is extended or adjusted under 35 U.S.C. 154(b) by 559 days.

(21) Appl. No.: 16/074,575

(22) PCT Filed: Jan. 31, 2017

(86) PCT No.: PCT/EP2017/051980
§ 371 (c)(1),
(2) Date: Aug. 1, 2018

(87) PCT Pub. No.: WO2017/134026
PCT Pub. Date: Aug. 10, 2017

(65) Prior Publication Data
US 2019/0040263 A1 Feb. 7, 2019

(30) Foreign Application Priority Data

Feb. 1, 2016 (EP) .................................. 16305104
Oct. 7, 2016 (EP) .................................. 16306325

(51) Int. Cl.
*C09C 1/02* (2006.01)
*C09C 1/24* (2006.01)
*C09C 1/28* (2006.01)
*C09C 1/30* (2006.01)
*C09C 1/34* (2006.01)
*C09C 1/36* (2006.01)
*C09C 1/40* (2006.01)
*C09C 1/42* (2006.01)
*C09C 3/04* (2006.01)
*C09C 3/08* (2006.01)
*C08L 27/06* (2006.01)
*C08L 23/06* (2006.01)
*C08L 23/12* (2006.01)
*A61L 31/02* (2006.01)
*A61L 31/12* (2006.01)
*A61L 15/18* (2006.01)
*C08K 3/26* (2006.01)
*C08K 9/04* (2006.01)
*C08L 67/02* (2006.01)

(52) U.S. Cl.
CPC ............. *C09C 1/021* (2013.01); *A61L 15/18* (2013.01); *A61L 31/02* (2013.01); *A61L 31/128* (2013.01); *C08K 3/26* (2013.01); *C08K 9/04* (2013.01); *C08L 23/06* (2013.01); *C08L 23/12* (2013.01); *C08L 27/06* (2013.01); *C08L 67/02* (2013.01); *C09C 1/02* (2013.01); *C09C 1/025* (2013.01); *C09C 1/027* (2013.01); *C09C 1/24* (2013.01); *C09C 1/28* (2013.01); *C09C 1/3009* (2013.01); *C09C 1/346* (2013.01); *C09C 1/3615* (2013.01); *C09C 1/407* (2013.01); *C09C 1/42* (2013.01); *C09C 3/04* (2013.01); *C09C 3/08* (2013.01); *C01P 2004/51* (2013.01); *C01P 2004/61* (2013.01); *C01P 2004/62* (2013.01); *C08K 2003/265* (2013.01); *C08K 2201/005* (2013.01); *C08L 2203/16* (2013.01)

(58) Field of Classification Search
None
See application file for complete search history.

(56) References Cited

U.S. PATENT DOCUMENTS

| 4,170,658 | A | 10/1979 | Skinner et al. |
|---|---|---|---|
| 4,732,748 | A | 3/1988 | Stewart et al. |
| 6,348,536 | B1 | 2/2002 | Fourty et al. |
| 6,569,527 | B1 | 5/2003 | Calhoun et al. |
| 8,647,597 | B1 | 2/2014 | Rainer |
| 2002/0155055 | A1 | 10/2002 | Denholm et al. |
| 2003/0039851 | A1 | 2/2003 | Hale et al. |
| 2004/0186193 | A1 | 9/2004 | Schamberg et al. |
| 2010/0035076 | A1 | 2/2010 | Kostuch et al. |
| 2012/0264865 | A1 | 10/2012 | Shaw et al. |
| 2014/0287185 | A1 | 9/2014 | Moseley et al. |
| 2014/0329945 | A1 | 11/2014 | Tranninger |
| 2015/0083831 | A1 | 3/2015 | Shaw et al. |
| 2015/0183963 | A1 | 7/2015 | Maeba et al. |

FOREIGN PATENT DOCUMENTS

| AU | B-3908389 | 2/1990 |
|---|---|---|
| CA | 2 927 899 A1 | 5/2015 |
| EP | 0 246 406 A2 | 11/1987 |
| EP | 0359 385 A1 | 3/1990 |
| EP | 0 614 948 A1 | 9/1994 |
| EP | 1 908 803 A2 | 4/2008 |
| EP | 2 592 054 A1 | 5/2013 |
| EP | 2 662 419 A1 | 11/2013 |
| EP | 2 933 298 A1 | 10/2015 |
| EP | 2 966 129 A1 | 1/2016 |
| EP | 3 002 318 A1 | 4/2016 |
| EP | 3 260 489 A1 | 12/2017 |
| JP | 2009-524541 A | 7/2009 |
| JP | 2015-504450 A | 2/2015 |

(Continued)

OTHER PUBLICATIONS

International Search Report and Written Opinion dated Jun. 7, 2017, in International Application No. PCT/EP2017/051980 (21 pgs.).

(Continued)

*Primary Examiner* — Daniel Berns
(74) *Attorney, Agent, or Firm* — Finnegan, Henderson, Farabow, Garrett & Dunner, LLP

(57) ABSTRACT

The present invention relates to an inorganic particulate material suitable for use in polymeric films, compositions such as polymeric films comprising the inorganic particulate materials, methods of making said compositions and the various uses of the inorganic particulate materials and compositions.

19 Claims, No Drawings

(56) References Cited

FOREIGN PATENT DOCUMENTS

| WO | WO 97/34956 | 9/1997 |
|---|---|---|
| WO | WO 99/61521 | 12/1999 |
| WO | WO 01/85832 A2 | 11/2001 |
| WO | WO 2004/016566 A1 | 2/2004 |
| WO | WO 2008/077156 A2 | 6/2008 |
| WO | WO 2010/034515 A1 | 4/2010 |
| WO | WO 2013/061068 A1 | 5/2013 |
| WO | WO 2014/060286 A1 | 4/2014 |
| WO | WO 2014/062476 A1 | 4/2014 |
| WO | WO 2017/011341 A1 | 1/2017 |

OTHER PUBLICATIONS

Bloodworth et al., "Industrial Minerals Laboratory Manual: Kaolin," British Geological Survey (1993).
$CaCO_3$ White Paper, Flexible Intermediate Bulk Container Association (2014).
Comex ACX Air Classifier (2016).
FiberLink™ 101S, Surface Modified Calcium Carbonate (2008).
Filmlink® 500, Engineered Minerals for the Film Industry (2010).
Gantenbein et al., "Determining the size distribution-defined aspect ratio of platy particles," Applied Clay Science (2011).
Hubercarb® W4 Calcium Carbonate, Huber (2013).
Imerys Annual Report 2004 (2005).
Jetfine® 3 C A Product Data Sheet (2011).
Jilkén et al., "The Effect of Mineral Fillers on Impact and Tensile Properties of Polypropylene," Polymer Testing, 10:329-344 (1991).
Luzenac A7 Data Sheet (2001).
Marras et al., "Recovery and Reuse of Marble Powder By-Product," Global Stone Congress (2010).
Omyabond® 520—FL (2009).
Omyabond® 700—FL (2012).
Omyacarb® 1—SJ (2009).
PCC Calciumcarbonat Technical Data Sheet (2000).
Talc CM1P Technical data sheet, Imifabi (2008).
Talc CM05P Technical data sheet, Imifabi (2008).
Talc HTP1 Technical data sheet, Imifabi (2008).
Talc HTP1c Technical datasheet, Imifabi (2008).
Talc HTP1 L Technical data sheet, Imifabi (2008).
Talc HTP05 Technical datasheet, Imifabi (2008).
Talc HTP05c Technical data sheet, Imifabi (2008).
Talc HTP05L Technical data sheet, Imifabi (2008).
Talc HTPultrat10 Technical data sheet, Imifabi (2008).
Talc HTPultrat10c Technical data sheet, Imifabi (2008).
Talc HTPultra10L Technical data sheet, Imifabi (2008).
TAPPI Monograph Series No. 30, "Paper Coating Pigments," (1966).
Vučak et al., "Application of Novel Plate-Shaped Calcium Carbonate in Inkjet Paper Coating," ipw, Das Papier (2004).

US 11,639,441 B2

INORGANIC PARTICULATE MATERIAL SUITABLE FOR USE IN POLYMERIC FILMS

CLAIM FOR PRIORITY

This application is a U.S. national phase entry under 35 U.S.C. § 371 from PCT International Application No. PCT/EP2017/051980, filed Jan. 31, 2017, which claims the benefit of priority of EP Application Nos. 16305104.8, filed Feb. 1, 2016, and 16306325.8, filed Oct. 7, 2016, from all of which this application claims priority and all of which are incorporated herein by reference.

TECHNICAL FIELD

The present invention relates generally to an inorganic particulate material (for example an alkali earth metal carbonate such as calcium carbonate) suitable for use in polymeric compositions, for example polymeric films, which may have high mineral loading. The present invention further relates to compositions comprising the inorganic particulate material, in particular polymers such as polymeric films comprising the inorganic particulate material. The present invention also relates to the use of the inorganic particulate material in polymeric compositions such as polymeric film and methods of making polymeric compositions such as polymeric films comprising the inorganic particulate material. Certain embodiments of the present invention relate to breathable polymeric films (e.g. films that allow the transmission of gas and vapours).

BACKGROUND OF THE INVENTION

Inorganic particulate materials such as calcium carbonate are used for numerous applications. One such use is the use in polymer compositions. The inorganic particulate material may be used as a filler (e.g. to reduce the amount of polymer required in the composition, for example to reduce the cost of the composition), or may affect the properties of the polymer.

For example, inorganic particulate materials may be used in polymeric films. Such films, porous or non-porous, are manufactured for a number of consumer products such as garbage bags, backing materials or outer covers on diapers, bandages, training pants, sanitary napkins, surgical drapes and surgical gowns. Polymeric films comprising polymer, inorganic particulate material and optional additives such as bonding or tackifying agent(s) may be formed by mixing (e.g. compounding) these components and then forming the resultant composition into a film layer using any one of a variety of film-producing processes known to those of ordinary skill in the art (e.g. by casting, blowing or extrusion). If the film is to be a porous, breathable film, the film can be stretched, uniaxially or biaxially, by any of the well-known techniques in the art including hydraulics, pinch rolls moving at different rates and tentering.

The nature and amount of the inorganic particulate material used in a polymeric film may influence the properties of the film, for example pore size (and therefore degree of breathability), strength, thickness and flexibility. The nature of the inorganic particulate material can also influence how easily and quickly the film can be processed. Decreasing the particle size of the inorganic particulate material may allow thinner films to be produced. However, this may cause issues with rheology of the polymeric melts and processing the polymeric films, for example increasing the running time. For example, decreasing the particle size of the inorganic particulate material may result in increased tension to be applied to the melt as it emerges from the die, which may, for example, increase the likelihood of developing holes in the melt.

Decreasing the particle size of the inorganic particulate material may also cause processing issues in the formation of other polymer products such as polymer fibres, for example by increasing the viscosity of a polymer melt (e.g. at high filler loadings). For example, swelling of the polymer melt as it emerges from a spinarette, causing a build-up of material on the die which may create drips and failure of the non-woven fibre web.

Incorporating the inorganic particulate material into the polymeric film, in particular at high loading levels and/or into thin films, may result in the inorganic particulate material being liberated from the film and being deposited on the film surface ("dusting"). This may, for example, be detrimental to the post-production conversion process, for example during the printing or lamination of the films to other structures (e.g. during the production of diapers).

It is therefore desirable to provide alternative and/or improved inorganic particulate materials that are suitable for use in polymer compositions such as polymeric films

SUMMARY OF THE INVENTION

In accordance with a first aspect of the present invention there is provided an inorganic particulate material (a) having a $d_{98}$ of less than about 11 µm or less than about 8 µm; and/or (b) comprising equal to or more than about 3 ppm of particles having a particle size equal to or greater than about 40 µm; and/or (c) comprising equal to or less than about 40 wt % of particles smaller than about 0.75 µm.

Thus, in a further aspect of the present invention there is provided an inorganic particulate material having a $d_{98}$ of less than about 11 µm or less than about 8 µm and comprising equal to or more than about 3 ppm of particles having a particle size equal to or greater than about 40 µm.

Thus, in a further aspect of the present invention there is provided an inorganic particulate material comprising equal to or more than about 3 ppm of particles having a particle size equal to or greater than about 40 µm and equal to or less than about 40 wt % of particles smaller than about 0.75 µm.

Thus, in a further aspect of the present invention there is provided an inorganic particulate material having a $d_{98}$ of less than about 11 µm or less than about 8 µm and comprising equal to or less than about 40 wt % of particles smaller than about 0.75 µm.

In certain embodiments, the inorganic particulate material has not undergone dry sieving or sifting. Thus, in a further aspect of the present invention there is provided an inorganic particulate material having a $d_{98}$ of less than about 11 µm or equal to or less than about 8 µm, wherein the inorganic particulate material has not undergone a dry sieving or sifting.

In certain embodiments, the inorganic particulate material comprises equal to or more than about 3 ppm of particles having a particle size equal to or greater than about 25 µm. Thus, in a further aspect of the present invention there is provided an inorganic particulate material having a $d_{98}$ of less than about 11 µm or equal to or less than about 8 µm and comprising equal to or more than about 3 ppm of particles having a particle size equal to or greater than about 3 ppm.

In accordance with a second aspect of the present invention there is provided a composition comprising an inorganic particulate material according to any aspect or embodiment of the present invention.

In accordance with a third aspect of the present invention there is provided a composition comprising a polymer and an inorganic particulate material according to any aspect or embodiment of the present invention. In certain embodiments, the composition may be a polymeric film (e.g. lamination coating such as LDPE lamination coating) or synthetic paper or raffia.

In accordance with a fourth aspect of the present invention there is provided a polymeric film comprising a polymer and an inorganic particulate material according to any aspect or embodiment of the present invention.

In accordance with a fifth aspect of the present invention there is provided a use of an inorganic particulate material according to any aspect or embodiment of the present invention in a polymer composition such as a polymeric film (e.g. lamination coating such as LDPE lamination coating), synthetic paper or raffia.

In accordance with a sixth aspect of the present invention there is provided a method for making a polymeric film, the method comprising:
  mixing (e.g. compounding) a polymer and an inorganic particulate material according to any aspect or embodiment of the present invention; and
  shaping the compounded material into a film.

In accordance with a seventh aspect of the present invention there is provided a use of an inorganic particulate material according to any aspect or embodiment of the present invention as a cavitation agent.

In accordance with an eighth aspect of the present invention there is provided a use of an inorganic particulate material according to any aspect or embodiment of the present invention in a polymeric film to reduce liberation of inorganic particulate material from the polymeric film and/or reduce deposition of inorganic particulate material on the polymeric film surface (dusting). This may, for example, be in comparison to a polymeric film that is identical except that it does not comprise the inorganic particulate material according to any aspect or embodiment of the present invention.

In certain embodiments of any aspect of the present invention, the inorganic particulate material comprises equal to or greater than about 3 ppm of particles having a particle size equal to or greater than about 25 µm.

In certain embodiments of any aspect of the present invention, the inorganic particulate material comprises equal to or greater than about 3 ppm of particles having a particle size equal to or greater than about 40 µm.

In certain embodiments of any aspect of the present invention, the inorganic particulate material comprises equal to or less than about 40 wt % of particles smaller than about 0.75 µm.

In certain embodiments of any aspect of the present invention, the inorganic particulate material has a $d_{98}$ equal to or less than about 11 µm or equal to or less than about 8 µm.

In certain embodiments of any aspect of the present invention, the inorganic particulate material has not undergone dry sieving or sifting.

In certain embodiments of any aspect of the present invention, the inorganic particulate material is an alkali earth metal carbonate such as calcium carbonate. In certain embodiments of any aspect of the present invention, the inorganic particulate material has a $d_{50}$ ranging from about 0.5 µm to about 3 µm. In certain embodiments of any aspect of the present invention, the inorganic particulate material has a $d_{50}$ ranging from about 0.5 µm to about 2.5 µm.

In certain embodiments of any aspect of the present invention, the polymer composition is a polymeric film (e.g. lamination coating such as LDPE lamination coating). In certain embodiments of any aspect of the present invention, the polymeric film is breathable.

Certain embodiments of the present invention may provide one or more of the following advantages:
  reduce the average particle size of the particulate material;
  reduce the % of ultra-fine particles (particles smaller than 0.75 µm) in the inorganic particulate material;
  reduce the $d_{98}$ top-cut of the inorganic particulate material;
  increase the steepness of the particle size distribution;
  increase the % of very coarse particles (e.g. larger than 20 µm);
  reduce or eliminate sifting of the inorganic particle prior to incorporation in the polymeric films;
  maintain or improve the dispersion of the inorganic particulate material;
  maintain or decrease the moisture pick-up of the inorganic particulate material;
  downgauging (production of thinner films);
  maintain or increase the breathability (e.g. MVTR) of the film;
  maintain the strength and flexibility of the film;
  lower level of "volatile" components in the film at high processing temperatures;
  improve processing of polymeric compositions (e.g. masterbatches or fibres or polymeric films (e.g. by reduce running time));
  allow for faster line speeds in producing the inorganic particulate material and/or the polymeric films;
  retention of the inorganic particulate material in the polymeric films (i.e. reduction of "dusting");
  improved cavitation agent for breathable films.

The details, examples and preferences provided in relation to any particular one or more of the stated aspects of the present invention apply equally to all aspects of the present invention. Any combination of the embodiments, examples and preferences described herein in all possible variations thereof is encompassed by the present invention unless otherwise indicated herein, or otherwise clearly contradicted by context.

DETAILED DESCRIPTION OF THE INVENTION

Inorganic Particulate Material

An inorganic particulate material suitable for use in polymeric compositions such as polymeric films is disclosed herein. In certain embodiments, the inorganic particulate material comprises equal to or greater than about 3 ppm of particles having a particle size equal to or greater than about 25 µm. In certain embodiments, the inorganic particulate material comprises equal to or greater than about 3 ppm of particles having a particle size equal to or greater than about 40 µm. In certain embodiments, the inorganic particulate material has not undergone dry sieving or sifting. The inorganic particulate material may have a $d_{98}$ of less than about 11 µm or less than about 8 µm. Inorganic particulate materials having these particle size properties have advantageously been found to be suitable for use in polymer compositions such as polymeric films. In particular, these inorganic particulate materials have been useful in downgauging of polymeric films without causing processing issues such as increasing of running time for the formation of the films. In particular, these inorganic particulate materials have been useful in reducing the viscosity of polymer melts, for example at high loading concentrations (e.g. more than 50 wt %). Surprisingly, it has been found that these advantageous properties are maintained when the inorganic particulate material includes some very coarse particles (e.g. particles equal to or greater than about 25 μm or equal to or greater than about 40 μm).

The inorganic particulate material may comprise equal to or greater than about 3 ppm of particles having a particle size equal to or greater than about 25 μm. In certain embodiments, the inorganic particulate material comprises equal to or greater than about 5 ppm of particles having a particle size equal to or greater than about 25 μm, for example equal to or greater than about 10 ppm, for example equal to or greater than about 20 ppm, for example equal to or greater than about 50 ppm of particles having a particle size equal to or greater than about 25 μm. In certain embodiments, the inorganic particulate material comprises equal to or greater than about 0.01 wt % of particles having a particle size equal to or greater than about 25 μm, for example equal to or greater than about 0.02 wt %, for example equal to or greater than about 0.03 wt %, for example equal to or greater than about 0.04 wt %, for example equal to or greater than about 0.05 wt % of particles having a particle size equal to or greater than about 25 μm.

In certain embodiments, the inorganic particulate material comprises up to about 1.5 wt % of particles having a particle size equal to or greater than about 25 μm. In certain embodiments, the inorganic particulate material comprises up to about 1 wt %, for example up to about 0.9 wt %, for example up to about 0.8 wt %, for example up to about 0.7 wt %, for example up to about 0.6 wt %, for example up to about 0.5 wt %, for example up to about 0.4 wt % of particles having a particle size equal to or greater than about 25 μm.

The inorganic particulate material may comprise equal to or greater than about 3 ppm of particles having a particle size equal to or greater than about 40 μm. In certain embodiments, the inorganic particulate material comprises equal to or greater than about 5 ppm of particles having a particle size equal to or greater than about 40 μm, for example equal to or greater than about 10 ppm, for example equal to or greater than about 20 ppm, for example equal to or greater than about 50 ppm of particles having a particle size equal to or greater than about 40 μm. In certain embodiments, the inorganic particulate material comprises equal to or greater than about 0.01 wt % of particles having a particle size equal to or greater than about 40 μm, for example equal to or greater than about 0.02 wt %, for example equal to or greater than about 0.03 wt %, for example equal to or greater than about 0.04 wt %, for example equal to or greater than about 0.05 wt % of particles having a particle size equal to or greater than about 40 μm.

In certain embodiments, the inorganic particulate material comprises up to about 1.5 wt % of particles having a particle size equal to or greater than about 40 μm. In certain embodiments, the inorganic particulate material comprises up to about 1 wt %, for example up to about 0.9 wt %, for example up to about 0.8 wt %, for example up to about 0.7 wt %, for example up to about 0.6 wt %, for example up to about 0.5 wt %, for example up to about 0.4 wt % of particles having a particle size equal to or greater than about 40 μm.

The inorganic particulate material may comprise equal to or greater than about 3 ppm of particles having a particle size equal to or greater than about 38 μm or about 30 μm or about 25 μm or about 20 μm. In certain embodiments, the inorganic particulate material comprises equal to or greater than about 5 ppm of particles having a particle size equal to or greater than about 38 μm or about 30 μm or about 25 μm or about 20 μm, for example equal to or greater than about 10 ppm, for example equal to or greater than about 20 ppm, for example equal to or greater than about 50 ppm of particles having a particle size equal to or greater than about 38 μm or about 30 μm or about 25 μm or about 20 μm. In certain embodiments, the inorganic particulate material comprises equal to or greater than about 0.01 wt % of particles having a particle size equal to or greater than about 38 μm or about 30 μm or about 25 μm or about 20 μm, for example equal to or greater than about 0.02 wt %, for example equal to or greater than about 0.03 wt %, for example equal to or greater than about 0.04 wt %, for example equal to or greater than about 0.05 wt % of particles having a particle size equal to or greater than about 38 μm or about 30 μm or about 25 μm or about 20 μm.

In certain embodiments, the inorganic particulate material comprises up to about 2 wt % of particles having a particle size equal to or greater than about 38 μm or about 30 μm or about 25 μm or about 20 μm. In certain embodiments, the inorganic particulate material comprises up to about 1 wt %, for example up to about 0.9 wt %, for example up to about 0.8 wt %, for example up to about 0.7 wt %, for example up to about 0.6 wt %, for example up to about 0.5 wt %, for example up to about 0.4 wt % of particles having a particle size equal to or greater than about 38 μm or about 30 μm or about 25 μm or about 20 μm.

The inorganic particulate material may have a $d_{98}$ (top-cut) of less than about 11 μm. In certain embodiments, the inorganic particulate material has a $d_{98}$ equal to or less than about 10 μm, for example less than about 9 μm, for example less than about 8 μm, for example less than about 7.5 μm, for example equal to or less than about 7 μm, for example equal to or less than about 6.5 μm, for example equal to or less than about 6 μm, for example equal to or less than about 5.5. μm, for example equal to or less than about 5 μm. In certain embodiments, the inorganic particulate material has a $d_{98}$ ranging from about 3 μm to about 11 μm or from about 3 μm to about 10 μm or from about 3 μm to about 9 μm or from about 3 μm to about 8 μm, for example from about 3.5 μm to about 7 μm, for example from about 4 μm to about 6 μm, for example from about 4.5 μm to about 5.5 μm, for example about 5 μm.

The inorganic particulate material may, for example, have a $d_{50}$ ranging from about 0.5 μm to about 3 μm, for example from about 0.5 μm to about 2.75 μm, for example from about 0.5 μm to about 2.5 μm, for example from about 0.75 μm to about 2.2 μm, for example from about 0.8 μm to about 2 μm. In certain embodiments, the inorganic particulate material has a $d_{50}$ ranging from about 0.5 μm to about 1.5 μm, for example from about 0.6 μm to about 1.4 μm, for example from about 0.7 μm to about 1.3 μm, for example from about 0.75 μm to about 1.25 μm, for example from about 0.8 μm to about 1.2 μm, for example from about 0.9 μm to about 1.1 μm, for example about 1 μm. In certain embodiments, the inorganic particulate material has a $d_{50}$ ranging from about 1 μm to about 2.5 μm, for example from about 1.5 μm to about 2.5 μm, for example from about 1.5 μm to about 2 μm, for example from about 1.7 μm to about 2 μm.

The % of inorganic particulate material particles smaller than 0.75 μm may, for example, be equal to or less than about 40 wt %, for example equal to or less than about 39 wt %, for example equal to or less than about 38 wt %, for example equal to or less than about 37 wt %, for example equal to or less than about 36 wt %, for example equal to or less than about 35 wt %. In certain embodiments, the % of inorganic particulate material particles smaller than 0.75 μm is equal to or less than about 25 wt %, for example equal to or less than about 24 wt %, for example equal to or less than about 23 wt %, for example equal to or less than about 22 wt %, for example equal to or less than about 21 wt %, for example equal to or less than about 20 wt %. In certain embodiments, the % of particles smaller than 0.75 μm may be equal to or greater than about 1 wt %, for example equal to or greater than about 2 wt %, for example equal to or greater than about 5 wt %.

The % of inorganic particulate material particles smaller than 0.5 μm may, for example, be equal to or less than about 25 wt %, for example equal to or less than about 24 wt %, for example equal to or less than about 23 wt %, for example equal to or less than about 22 wt %, for example equal to or less than about 21 wt %, for example equal to or less than about 20 wt %. In certain embodiments, the % of inorganic particulate material particles smaller than 0.5 μm is equal to or less than about 15 wt %, for example equal to or less than about 14 wt %, for example equal to or less than about 13 wt %, for example equal to or less than about 12 wt %. In certain embodiments, the % of particles smaller than 0.5 μm may be equal to or greater than about 1 wt %, for example equal to or greater than about 2 wt %, for example equal to or greater than about 5 wt %.

The % of inorganic particulate material particles smaller than 5 μm may, for example, range from about 85 wt % to about 99 wt %, for example from about 90 wt % to about 99 wt %. In certain embodiments, the % of particles smaller than about 5 μm may range from about 85 wt % to about 95 wt %, for example from about 90 wt % to about 95 wt %. In certain embodiments, the % of particles smaller than about 5 μm may range from about 90 wt % to about 99 wt %, for example from about 95 wt % to about 99 wt %.

The % of inorganic particulate material particles smaller than 2 μm may, for example, range from about 40 wt % to about 95 wt %, for example from about 45 wt % to about 90 wt %, for example from about 50 wt % to about 90 wt %. In certain embodiments, the % of particles smaller than 2 μm may range from about 40 wt % to about 70 wt %, for example from about 45 wt % to about 65 wt %, for example from about 50 wt % to about 60 wt %. In certain embodiments, the % of particles smaller than 2 μm may range from about 70 wt % to about 95 wt %, for example from about 75 wt % to about 90 wt %, for example from about 80 wt % to about 90 wt %.

The % of inorganic particulate material particles smaller than 1 μm may, for example, range from about 15 wt % to about 65 wt %, for example from about 20 wt % to about 60 wt %, for example from about 25 wt % to about 55 wt %. In certain embodiments, the % of particles smaller than 1 μm may range from about 15 wt % to about 40 wt %, for example from about 15 wt % to about 35 wt %, for example from about 20 wt % to about 35 wt %, for example from about 20 wt % to about 30 wt %. In certain embodiments, the % of particles smaller than 1 μm may range from about 30 wt % to about 60 wt %, for example from about 40 wt % to about 60 wt %, for example from about 45 wt % to about 55 wt %.

The inorganic particulate material may, for example, have a steepness factor of at least about 35. For example, the inorganic particulate material may have a steepness factor ranging from about 35 to about 55, for example from about 40 to about 50, for example from about 41 to about 49, for example from about 42 to about 48, for example from about 43 to about 47, for example from about 44 to about 46, for example about 45. Steepness factor is defined as $(d_{30}/d_{70}) \times 100$.

In certain embodiments, the inorganic particulate material has a $d_{98}$ of less than about 8 μm, a $d_{50}$ ranging from about 0.5 μm to about 1.5 μm, a % of particles smaller than 5 μm ranging from about 90 wt % to about 99 wt %, a % of particles smaller than 2 μm ranging from about 75 wt % to about 95 wt % and a % of particles smaller than 1 μm ranging from about 40 wt % to about 60 wt %.

In certain embodiments, the inorganic particulate material has a $d_{98}$ of less than about 6 μm, a $d_{50}$ ranging from about 0.75 μm to about 1.25 μm, a % of particles smaller than 5 μm ranging from about 95 wt % to about 99 wt %, a % of particles smaller than 2 μm ranging from about 80 wt % to about 90 wt % and a % of particles smaller than 1 μm ranging from about 44 wt % to about 55 wt %.

In certain embodiments, the inorganic particulate material has a $d_{98}$ of less than about 5 μm, a $d_{50}$ of about 1 μm, a % of particles smaller than 5 μm ranging from about 96 wt % to about 99 wt %, a % of particles smaller than 2 μm ranging from about 82 wt % to about 88 wt % and a % of particles smaller than 1 μm ranging from about 47 wt % to about 53 wt %.

In certain embodiments, the inorganic particulate material has a $d_{98}$ of less than about 8 μm, a $d_{50}$ ranging from about 1 μm to about 2.5 μm, a % of particles smaller than 5 μm ranging from about 90 wt % to about 99 wt %, a % of particles smaller than 2 μm ranging from about 45 wt % to about 65 wt % and a % of particles smaller than 1 μm ranging from about 20 wt % to about 35 wt %.

In certain embodiments, the inorganic particulate material has a $d_{98}$ of less than about 7 μm, a $d_{50}$ ranging from about 1.5 μm to about 2 μm, a % of particles smaller than 5 μm ranging from about 90 wt % to about 97 wt %, a % of particles smaller than 2 μm ranging from about 50 wt % to about 60 wt % and a % of particles smaller than 1 μm ranging from about 22 wt % to about 32 wt %.

In certain embodiments, the inorganic particulate material has a $d_{98}$ of less than about 7 μm, a $d_{50}$ ranging from about 1.7 to about 1.9 μm, a % of particles smaller than 5 μm ranging from about 92 wt % to about 97 wt %, a % of particles smaller than 2 μm ranging from about 52 wt % to about 58 wt % and a % of particles smaller than 1 μm ranging from about 24 wt % to about 30 wt %.

The % of particles smaller than 0.25 μm may, for example, be equal to or less than about 10 wt %, for example equal to or less than about 9 wt %, for example equal to or less than about 8 wt %, for example equal to or less than about 7 wt %, for example equal to or less than about 6 wt %, for example equal to or less than about 4 wt %. The % of particles smaller than 0.25 μm may, for example, be at least about 1 wt %.

The % of particles smaller than 0.1 μm may, for example, be equal to or less than about 5 wt %, for example equal to or less than about 4 wt %, for example equal to or less than about 3 wt %, for example equal to or less than about 2 wt %. The % of particles smaller than 0.1 μm may, for example, be at least about 0.1 wt %.

Unless otherwise stated, particle size properties referred to herein for the inorganic particulate materials are as measured in a well known manner by sedimentation of the particulate filler or material in a fully dispersed condition in an aqueous medium using a Sedigraph 5100 machine as supplied by Micromeritics Instruments Corporation, Norcross, Ga., USA (telephone: +17706623620; web-site: www.micromeritics.com), referred to herein as a "Micromeritics Sedigraph 5100 unit". Such a machine provides measurements and a plot of the cumulative percentage by weight of particles having a size, referred to in the art as the 'equivalent spherical diameter' (e.s.d), less than given e.s.d values. The mean particle size $d_{50}$ is the value determined in this way of the particle e.s.d at which there are 50% by weight of the particles which have an equivalent spherical diameter less than that $d_{50}$ value. The $d_{98}$ and the $d_{90}$ are the values determined in this way of the particle e.s.d. at which there are 98% and 90% respectively by weight of the particles which have an equivalent spherical diameter less than that $d_{98}$ or $d_{90}$ value. Unless otherwise stated, particle size properties referred to herein refer to the particle size properties of the inorganic particulate materials prior to any surface treatment (i.e. without coating).

The desired particle size distribution may, for example, be obtained by any suitable method known to those skilled in the art. For example, the desired particle size distribution may be obtained using one or more of the following methods, dry sieving or sifting, removal of fine particles before they become "overground" (e.g. using hydrocyclone), removing particles from dry products by air-classification, Ostwald ripening process.

The inorganic particulate material may, for example, be alkali earth metal carbonate, (for example dolomite, i.e. $CaMg(CO_3)_2$, or calcium carbonate), metal sulphate, (for example barite or gypsum), metal silicate, metal oxide (for example titania, iron oxide, chromia, antimony trioxide or silica), metal hydroxide (for example alumina trihydrate), kaolin, calcined kaolin, wollastonite, bauxite, talc or mica, including combinations thereof. For example, the inorganic particulate material may be an alkali earth metal carbonate such as calcium carbonate. Hereinafter, the present invention may tend to be discussed in terms of calcium carbonate. However, the invention should not be construed as being limited to calcium carbonate.

The particulate calcium carbonate used in the present invention may be obtained from a natural source by grinding or may be prepared synthetically by precipitation (PCC), or may be a combination of the two, i.e. a mixture of the naturally derived ground material and the synthetic precipitated material. The PCC may also be ground.

Ground calcium carbonate (GCC), i.e. ground natural calcium carbonate is typically obtained by grinding a mineral source such as chalk, marble or limestone, which may be followed by a particle size classification step, in order to obtain a product having the desired degree of fineness. The particulate solid material may be ground autogenously, i.e. by attrition between the particles of the solid material themselves, or alternatively, in the presence of a particulate grinding medium comprising particles of a different material from the calcium carbonate to be ground.

Wet grinding of calcium carbonate involves the formation of an aqueous suspension of the calcium carbonate which may then be ground, optionally in the presence of a suitable dispersing agent. Reference may be made to, for example, EP-A-614948 (the contents of which are incorporated by reference in their entirety) for more information regarding the wet grinding of calcium carbonate.

When the filler is obtained from naturally occurring sources, it may be that some mineral impurities will inevitably contaminate the ground material. For example, naturally occurring calcium carbonate occurs in association with other minerals. Also, in some circumstances, minor additions of other minerals may be included, for example, one or more of kaolin, calcined kaolin, wollastonite, bauxite, talc or mica, could also be present. In general, however, the filler used in the invention will contain less than 5% by weight, preferably less than 1% by weight of other mineral impurities.

PCC may be used as the source of particulate calcium carbonate in the present invention, and may be produced by any of the known methods available in the art. TAPPI Monograph Series No 30, "Paper Coating Pigments", pages 34-35 describes the three main commercial processes for preparing precipitated calcium carbonate which is suitable for use in preparing products for use in the paper industry, but may also be used in the practice of the present invention. In all three processes, limestone is first calcined to produce quicklime, and the quicklime is then slaked in water to yield calcium hydroxide or milk of lime. In the first process, the milk of lime is directly carbonated with carbon dioxide gas. This process has the advantage that no by-product is formed, and it is relatively easy to control the properties and purity of the calcium carbonate product. In the second process, the milk of lime is contacted with soda ash to produce, by double decomposition, a precipitate of calcium carbonate and a solution of sodium hydroxide. The sodium hydroxide must be substantially completely separated from the calcium carbonate if this process is to be commercially attractive. In the third main commercial process, the milk of lime is first contacted with ammonium chloride to give a calcium chloride solution and ammonia gas. The calcium chloride solution is then contacted with soda ash to produce, by double decomposition, precipitated calcium carbonate and a solution of sodium chloride.

The process for making PCC results in very pure calcium carbonate crystals and water. The crystals can be produced in a variety of different shapes and sizes, depending on the specific reaction process that is used. The three main forms of PCC crystals are aragonite, rhombohedral and scalenohedral, all of which are suitable for use in the present invention, including mixtures thereof.

Optionally, the inorganic particulate material may be surface-treated (coated). For example, the inorganic particulate material (e.g. calcium carbonate (GCC or PCC)) may be coated with a hydrophobising surface treatment agent such as an aliphatic compound. For example, the calcium carbonate may be coated with one or more aliphatic carboxylic acids or salts thereof having at least 10 chain carbon atoms. For example, the calcium carbonate may be coated with one or more fatty acids or salts or esters thereof. The fatty acids may be selected from stearic acid, palmitic acid, behenic acid, montanic acid, capric acid, lauric acid, myristic acid, isostearic acid and cerotic acid. The coated/surface-treated calcium carbonate may be a stearate coated calcium carbonate (e.g. ammonium stearate coated calcium carbonate). The inventors of the present invention have found that stearate coated calcium carbonate is particularly effective, even more particularly stearate coated GCC.

In certain embodiments, the level of coating is such that the inorganic particulate material is substantially in monolayer form. This may, for example, mean that there is a slight excess of coating. This may, for example, be advantageous in that the additional coating provides additional lubrication for the finer particles and there may, for example, be low levels of volatiles at high temperatures during processing of polymeric films. The level of coating may be about 0.5 wt % to about 1.5 wt %, for example about 0.8 wt % to about 1.3 wt % based on the dry weight of the particulate filler.

Other suitable coated or treated fillers include treated calcined kaolin and treated talc. The calcined kaolin may, for example, be treated with a silane (e.g. an organo-silane) or propylene glycol, while talc may be treated with a silane (e.g. an organo-silane).

The filler may be dried prior to inclusion in a composition. For example, the filler may be dried before being combined with a polymer resin. Typically, the filler may be dried in a conventional oven at about 80° C. The polymer may be dried in a vacuum oven at approximately 80° C. The particulate filler may be dried to an extent such that the particulate filler has and maintains an adsorbed water (or moisture) content not greater than about 0.5 wt %, for example and particularly advantageously, not greater than about 0.2 wt % or not greater than about 0.1 wt % based on the dry weight of the particulate filler. This includes both uncoated and coated particulate fillers. Low levels of adsorbed water are particularly beneficial when the filler is used to form breathable films.

Desirably, the particulate filler, including when either coated or uncoated, is not susceptible to further substantial moisture pick-up. The particulate filler may, for example, have a moisture level not greater than about 0.5 wt %, for example not greater than about 0.2 wt %, for example not greater than about 0.1 wt % after exposure to an atmosphere of 97% or more relative humidity for 48 hours at a temperature of 20° C.

The particulate filler may be free or substantially free of hygroscopic or hydrophilic compounds. For example, during grinding of the particulate filler, the grinding may be carried out in the absence of added hygroscopic or hydrophilic compounds, or if wet ground, any dispersant employed may be minimised and/or subsequently removed from the filler in a known manner. For example, not greater than about 0.05 wt % of a hydrophilic component may be present on the particulate filler based on the dry weight of the particulate filler. For example, not greater than about 0.05 wt % of a dispersant, for example, a hydrophilic dispersant, may be present on the particulate filler based on the dry weight of the particulate filler. An example of such a dispersant is sodium polyacrylate. The moisture level may be measured in a known manner, e.g. by a Karl Fischer (KF) titration apparatus. In this method, the water may be driven off from the sample by heating and then measured using the quantitative reaction of water with iodine. In coulometric KF titration, the sample is added to a pyridine-methanol solution (with iodine and sulphur dioxide as principal components). The iodine generated electrolytically at the anode, reacts with water. The amount of water can be directly determined from the quantity of electric charge required for electrolysis.

Compositions Comprising the Inorganic Particulate Material

Compositions comprising the inorganic particulate material disclosed herein (including all embodiments and combinations thereof) are also disclosed. The compositions may, for example, be an aqueous slurry. The compositions may, for example be polymer compositions comprising a polymer and the inorganic particulate material. The polymer compositions may, for example, be a polymeric film, a polymer fibre, a woven or nonwoven material, a synthetic paper (paper made partly or completely from synthetic polymer, for example having the properties of traditional paper such as folder and printing, but does not tear, puncture or absorb water as easily) or raffia (e.g. in raffia tape or woven raffia packaging) (e.g. polypropylene raffia). In certain embodiments, the inorganic particulate material is incorporated into a polymer film. In certain embodiments, the inorganic particulate material is incorporated into a lamination coating, for example a polyethylene lamination coating (e.g. low density polyethylene (LDPE) lamination coating). Advantageously, the inorganic particulate material is incorporated into a breathable polymer film.

The polymer film comprises a polymer and an inorganic particulate material. The polymer may be a homopolymer or a copolymer. Suitable polymers include thermoplastic resins such as polyolefin resin, for example, including mono-olefin polymers of ethylene, propylene, butene or the like, functionalized derivatives and physical blends and copolymers of the same. Typical examples of the polyolefin resin include polyethylene resins such as a low-density polyethylene, linear low density polyethylene (ethylene-a-olefin copolymer), middle-density polyethylene and high-density polyethylene; polypropylene resins such as polypropylene and ethylene-polypropylene copolymer; poly (4-methylpentene); polybutene; ethylene-vinyl acetate copolymer; polyvinyl chloride; polyethylene terephthalate; and mixtures thereof. These polyolefin resins may be obtained by polymerisation in a known way, e.g. by the use of a Ziegler catalyst, or obtained by the use of a single site catalyst such as a metallocene catalyst. In certain embodiments, the polymer film is biaxially oriented polypropylene (BOPP) or biaxially oriented polyethylene terephthalate (BOPET).

Before use, the polymer may be dried until a required level of dryness is attained. The inorganic particulate material may also be independently dried before mixing with the polymer.

Optionally, the polymer composition (e.g. polymer film) may further comprise one or more additives. Examples of useful additives include, but are not limited to, opacifying agents, pigments, colorants, slip agents, antioxidants, anti-fog agents, anti-static agents, anti-block agents, moisture barrier additives, gas barrier additives, hydrocarbon resins or hydrocarbon waxes. In certain embodiments, the polymer film further comprises a bonding or tackifying agent.

Optionally, the polymer composition (e.g. polymer film) may further comprise one or more additional inorganic particulate materials (not in accordance with the inorganic particulate materials of the invention). Additional fillers may, for example, be calcium carbonate, barium sulphate, calcium sulphate, barium carbonate, magnesium hydroxide, aluminium hydroxide, zinc oxide, magnesium oxide, titanium oxide, silica, talc, kaolin and combinations thereof.

The inorganic particulate material, which may or may not have been surface treated, may be incorporated in polymer compositions and is typically present at a concentration of about 1 wt % to about 80 wt %, for example from about 1 wt % to about 60 wt %, for example from about 2 to 55 wt % by weight of the final polymer film. For example, the inorganic particulate material may be incorporated in polymer compositions at a concentration of about 5 to 50 wt %, for example, about 10 to 25 wt %. For use in breathable films, the inorganic particulate material, which may or may not have been surface treated, may be incorporated in polymer compositions and is typically present at a concentration of about 30 wt % to about 55 wt % by weight of the final polymer film, for example, about 45 wt % to about 55 wt %.

The polymer may be incorporated in the composition is typically present at a concentration of about 45% to about 98% by weight of the final polymer composition (e.g. polymer film). For example, the polymer is typically present at a concentration of about 50% to about 95%, for example about 50% to about 90%, for example about 55% to about 90%, for example about 60% to about 85%, for example about 65% to about 80%, by weight of the final polymer composition (e.g. polymer film).

A film is a sheet or layer or material having an average thickness of up to 250 µm. The polymer film may, for example, have a thickness ranging from about 5 µm to about 250 µm. For example, the polymer film may have a thickness ranging from about 5 µm to about 50 µm, for example from about 5 µm to about 20 µm, for example from about 5 µm to about 15 µm, for example from about 5 µm to about 10 µm.

The polymer film may, for example, be a breathable polymer film in that it allows transmission of gases and vapours. The polymer film may, for example, have a moisture vapour transmission rate (MVTR) ranging from about 2000 gsm/day to about 15,000 gsm/day as calculated in accordance with ASTM E96/E96M-05. For example, the polymer film may have a MVTR of at least about 3000 gsm/day, for example at least about 4000 gsm/day, for example at least about 5000 gsm/day, for example at least about 6000 gsm/day. For example, the polymer film may have a MVTR ranging from about 5000 to about 15,000 gsm/day, for example from about 8000 to about 15,000 gsm/day, for example from about 10,000 to about 15,000 gsm/day, for example from about 11,000 to about 14,000 gsm/day, for example from about 11,000 to about 13,000 gsm/day, for example from about 11,000 to about 12,000 gsm/day.

The inorganic particulate material disclosed herein may be used in a polymeric film in order to reduce liberation of inorganic particulate material from the polymeric film and/or to reduce deposition of the inorganic particulate material on the polymeric film surface (dusting). The reduction may, for example, be in comparison to polymeric film that is identical except that it does not comprise an inorganic particulate material in accordance with any aspect or embodiment of the invention.

Methods of Making the Compositions

Methods of making the polymer compositions (e.g. polymer films) described herein are also disclosed. The polymer (resin) may be melted (or otherwise softened) prior to formation of the polymer composition (e.g. film), and the polymer will not normally be subjected to any further chemical transformations. After formation of the polymer composition (e.g. film), the polymer resin may be cooled and allowed to harden.

The polymer composition may be made by methods which are well known in the art generally in which a particulate filler and a polymer are mixed together in suitable ratios to form a blend (so-called "compounding"). The polymer may be in a liquid form to enable the particles of the filler to be dispersed therein. Where the polymers are solid at ambient temperatures, the polymer resin may need to be melted before the compounding can be accomplished. In some embodiments, the particulate filler may be dry blended with particles of the polymer, dispersion of the particles in the resin then being accomplished when the melt is obtained prior to forming a film from the melt, for example in an extruder itself.

In embodiments of the invention, the polymer and the particulate filler and, if necessary, any other optional additives, may be formed into a suitable masterbatch by the use of a suitable compounder/mixer in a manner known per se, and may be pelletized, e.g. by the use of a single screw extruder or a twin-screw extruder which forms strands which may be cut or broken into pellets. The compounder may have a single inlet for introducing the filler and the polymer resin together. Alternatively, separate inlets may be provided for the filler and the polymer resin. Suitable compounders are available commercially, for example from Coperion (formerly Werner & Pfleiderer).

The polymer compositions according to the present invention can be processed to form, or to be incorporated in, polymer films in any suitable way. Methods of making polymer films (e.g. lamination coatings) are well known to those of ordinary skill in the art and may be prepared in a conventional manner. Known methods include the use of casting, extruding and blowing processes. For example, extrusion blown film lines may be used. For those instances where combinations of polymers are used, then co-extrusion techniques may be used. Methods of co-extrusion are well known to the person of ordinary skill. Typically, two or more streams of molten polymer resin are joined into a single extrudate stream in such a way that the resins bond together but do not mix. Generally, a separate extruder is required for each stream and the extruders are linked so that the extrudates can flow together in an appropriate manner for the desired application. For making layered films, several extruders may be used in combination and fed together into a complex die that will merge each of the resin streams into a layered film or sandwich material.

The use of fillers in breathable films is described in WO 99/61521, U.S. Pat. No. 6,569,527 B1 and WO 2013/061068, the contents of which are incorporated herein in their entirety by reference.

In the manufacture of a breathable film a blend or masterbatch of the polymer (e.g. thermoplastic polyolefin resin) and the filler may first be produced by mixing and compounding prior to the film production stages. The mixture of ingredients to be blended by compounding may include, in addition to the resin and the particulate filler, other known optional ingredients employed in thermoplastic films, e.g. one or more of bonding or tackifying agents, plasticisers, lubricants, anti-oxidants, ultraviolet absorbers, dyes, colourants. A bonding or tackifying agent where employed may facilitate bonding of the film after formation to another member, e.g. a nonwoven fibrous layer, or one or more non porous layers.

The polymer, the filler and, if necessary, other optional additives, may be mixed by the use of a suitable compounder/mixer e.g. a Henschel mixer, a super mixer, a tumbler type mixer or the like, and kneaded and may be pelletized, e.g. by the use of a single screw extruder or a twin-screw extruder which forms strands which may be cut or broken into pellets. The masterbatch or blend, e.g. in the form of pellets, may be melted and moulded or shaped into a film by the use of a known moulding and film forming machine.

The film may be a blown film, cast film or extruded film. The film as initially formed may be generally too thick and too noisy as it tends to make a rattling sound when shaken and the film may not yet have a sufficient degree of breathability as measured by its water vapour transmission rate. Consequently, the film may be heated, e.g. to a temperature of about 5° C. less than the melting point of the thermoplastic polymer or more, and then stretched to at least about 1.2 times, for example at least about 2.5 times, its original length to thin the film and make it porous.

An additional feature of the thinning process is the change in opacity of the film. As formed, the film is relatively transparent but after stretching, it becomes opaque. In addition, while the film becomes orientated during the stretching process, it also becomes softer and it does not have the degree of rattle that it does prior to stretching. Taking all these factors into consideration, and the desire to have a water vapour transmission rate of, for example, at least 100 grams per square metre per 24 hours, the film may, for example, be thinned to such an extent that it has a weight per unit area of less than about 35 grams per square metre for personal care absorbent article applications and a weight per unit area of less than about 18 grams per square metre for certain other applications.

The moulding and film forming machine may, for example, comprise an extruder equipped with a T-die or the like or an inflation moulding machine equipped with a circular die. The film production may be carried out at some time after the masterbatch production, possibly at a different manufacturing plant. In some cases, the masterbatch can directly be formed into the film without producing an intermediate product, e.g. by pelletizing.

The film can be stretched in at least a uniaxial direction at a temperature of from room temperature to the softening point of the resin in a known manner such as a roll method or a tenter method to bring about the interfacial separation of the resin and the particulate filler from each other, whereby a porous film can be prepared. The stretching may be carried out by one step or by several steps. Stretch magnification determines film breakage at high stretching as well as breathability and the moisture vapour transmission of the obtained film, and so excessively high stretch magnification and excessively low stretch magnification are desirably avoided. The stretch magnification is preferably in the range of about 1.2 to 5 times, for example about 1.2 to 4 times in at least a uniaxial direction. If biaxial stretching is carried out, it is possible that, for example, stretching in a first direction is applied in the machine direction or a direction perpendicular thereto, and stretching in a second direction is then applied at right angles to the first direction. Alternatively, the biaxial stretching may be carried out simultaneously in the machine direction and the direction perpendicular thereto.

After the stretching, a heat setting treatment may be carried out if required in order to stabilise the shape of obtained voids. The heat setting treatment may be, for example, a heat setting treatment at a temperature in the range of from the softening point of the resin to a temperature less than the melting point of the resin for a period of about 0.1 to about 100 seconds. The thickness should preferably be such as to obtain film unlikely to tear or break and which has appropriate softness and good feel.

Uses of the Compositions

The porous, or breathable, film prepared in accordance with the present invention may have a suitable breathability, moisture vapour transmission and feeling as well as excellent mechanical properties and long-term adhesive properties. The breathable film may, for example, be suitably used in products such as disposable diapers, body fluid absorbing pads and bed sheets; medical materials such as surgical gowns and base materials for hot compress; clothing materials such as jumpers, rainwear; building materials such as wallpapers and waterproof materials for roofs and house wraps; packaging materials for packaging desiccants, dehumidifying agents, deoxidizers, insecticides, disposable body warmers; packaging materials for keeping the freshness of various articles and foods; separators for the cells; and the like. The breathable film is particularly desirable as a material used in products such as disposable diapers and body fluid absorbing pads. The breathable film may in such products be formed into a composite or laminate with one or more other layers, e.g. a nonwoven fibrous layer, e.g. by an adhesive or bonding agent.

For the avoidance of doubt, the present invention may be as defined in any one of the following numbered paragraphs:

1. An inorganic particulate material comprising:
   (a) equal to or more than about 3 ppm of particles having a particle size equal to or greater than about 40 μm and having a $d_{98}$ less than about 11 μm; or
   (b) equal to or more than about 3 ppm of particles having a particle size equal to or greater than about 40 μm and equal to or less than about 40 wt % of particles smaller than about 0.75 μm; or
   (c) equal to or less than about 40 wt % of particles smaller than about 0.75 μm and having a $d_{98}$ less than about 11 μm.
2. The inorganic particulate material of paragraph 1, comprising equal to or more than about 3 ppm of particles having a particle size equal to or greater than about 25 μm.
3. The inorganic particulate material of paragraph 1 or 2, comprising equal to or more than about 3 ppm of particles having a particle size equal to or greater than about 38 μm or equal to or greater than about 30 μm or equal to or greater than about 25 μm or equal to or greater than about 20 μm.
4. The inorganic particulate material of any one of paragraphs 1 to 3, having a $d_{50}$ ranging from about 0.5 to about 3 μm, for example from about 0.5 to about 2.5 μm.
5. The inorganic particulate material of any one of paragraphs 1 to 4, having a $d_{50}$ ranging from about 0.5 μm to about 1.5 μm, for example from about 0.75 μm to about 1.25 μm.
6. The inorganic particulate material of any one of paragraphs 1 to 5, having a $d_{50}$ ranging from about 1 μm to about 2.5 μm, for example from about 1.5 μm to about 2 μm.
7. The inorganic particulate material of any one of paragraphs 1 to 6, having a $d_{98}$ equal to or less than about 8 μm, for example equal to or less than about 7 μm, for example equal to or less than about 6 μm, for example equal to or less than about 5 μm.
8. The inorganic particulate material of any one of paragraphs 1 to 7, wherein the inorganic particulate material is an alkali earth metal carbonate.
9. The inorganic particulate material of any one of paragraphs 1 to 8, wherein the inorganic particulate material is calcium carbonate, for example ground calcium carbonate (GCC).
10. The inorganic particulate material of any one of paragraphs 1 to 9, having a steepness factor ranging from about 35 to about 50, for example ranging from about 40 to about 45.
11. The inorganic particulate material of any one of paragraphs 1 to 10, wherein the inorganic particulate material is surface-treated with a hydrophobising agent.
12. The inorganic particulate material of any one of paragraphs 1 to 11, wherein the inorganic particulate material is surface-treated with an aliphatic compound.
13. The inorganic particulate material of any one of paragraphs 1 to 12, wherein the inorganic particulate material is surface-treated with a fatty acid or salt thereof, for example stearic acid or a salt thereof.
14. The inorganic particulate material of any one of paragraphs 8 to 13, wherein the coating is substantially in monolayer form.
15. The inorganic particulate material of any one of paragraphs 1 to 14, having a moisture pick-up after 48 hours equal to or less than about 0.2 wt % at 97% relative humidity, for example equal to or less than about 0.1 wt % at 97% relative humidity.

16. The inorganic particulate material of any one of paragraphs 1 to 15, wherein the % of particles smaller than 0.75 µm is equal to or less than about 40 wt %, for example equal to or less than about 37 wt %.

17. The inorganic particulate material of any one of paragraphs 1 to 16, wherein the % of particles smaller than 0.5 µm is equal to or less than about 25 wt %, for example equal to or less than about 20 wt %, for example equal to or less than about 15 wt %.

18. An inorganic particulate material having a $d_{98}$ less than about 11 µm or equal to or less than about 8 µm, wherein the inorganic particulate material has not undergone dry sieving or sifting.

19. The inorganic particulate material of paragraph 18, comprising equal to or greater than about 3 ppm of particles having a particle size greater than or equal to about 25 µm.

20. The inorganic particulate material of paragraph 18 or 19, comprising equal to or more than about 3 ppm of particles having a particle size equal to or greater than about 40 µm.

21. The inorganic particulate material of any one of paragraphs 18 to 20, comprising equal to or more than about 3 ppm of particles having a particle size equal to or greater than about 38 µm or equal to or greater than about 30 µm or equal to or greater than about 25 µm or equal to or greater than about 20 µm.

22. The inorganic particulate material of any one of paragraphs 18 to 21, having a $d_{50}$ ranging from about 0.5 to about 3 µm, for example from about 0.5 to about 2.5 µm.

23. The inorganic particulate material of any one of paragraphs 18 to 22, having a $d_{50}$ ranging from about 0.5 µm to about 1.5 µm, for example from about 0.75 µm to about 1.25 µm.

24. The inorganic particulate material of any one of paragraphs 18 to 23, having a $d_{50}$ ranging from about 1 µm to about 2.5 µm, for example from about 1.5 µm to about 2 µm.

25. The inorganic particulate material of any one of paragraphs 18 to 24, having a $d_{98}$ equal to or less than about 8 µm, for example equal to or less than about 7 µm, for example equal to or less than about 6 µm, for example equal to or less than about 5 µm.

26. The inorganic particulate material of any one of paragraphs 18 to 25, wherein the inorganic particulate material is an alkali earth metal carbonate.

27. The inorganic particulate material of any one of paragraphs 18 to 26, wherein the inorganic particulate material is calcium carbonate, for example ground calcium carbonate (GCC).

28. The inorganic particulate material of any one of paragraphs 18 to 27, having a steepness factor ranging from about 35 to about 50, for example ranging from about 40 to about 45.

29. The inorganic particulate material of any one of paragraphs 18 to 28, wherein the inorganic particulate material is surface-treated with a hydrophobising agent.

30. The inorganic particulate material of any one of paragraphs 19 to 29, wherein the inorganic particulate material is surface-treated with an aliphatic compound.

31. The inorganic particulate material of any one of paragraphs 18 to 30, wherein the inorganic particulate material is surface-treated with a fatty acid or salt thereof, for example stearic acid or a salt thereof.

32. The inorganic particulate material of any one of paragraphs 18 to 31, wherein the coating is substantially in monolayer form.

33. The inorganic particulate material of any one of paragraphs 18 to 32, having a moisture pick-up after 48 hours equal to or less than about 0.2 wt % at 97% relative humidity, for example equal to or less than about 0.1 wt % at 97% relative humidity.

34. The inorganic particulate material of any one of paragraphs 18 to 33, wherein the % of particles smaller than 0.75 µm is equal to or less than about 40 wt %, for example equal to or less than about 37 wt %.

35. An inorganic particulate material having a $d_{98}$ of less than 11 µm and comprising equal to or more than about 3 ppm of particles having a particle size equal to or greater than about 25 µm.

36. The inorganic particulate material of paragraph 35, comprising equal to or more than about 3 ppm of particles having a particle size equal to or greater than about 40 µm.

37. The inorganic particulate material of paragraph 35 or 36, comprising equal to or more than about 3 ppm of particles having a particle size equal to or greater than about 38 µm or equal to or greater than about 30 µm or equal to or greater than about 25 µm or equal to or greater than about 20 µm.

38. The inorganic particulate material of any one of paragraphs 35 to 37, having a $d_{50}$ ranging from about 0.5 to about 3 µm, for example from about 0.5 to about 2.5 µm.

39. The inorganic particulate material of any one of paragraphs 35 to 38, having a $d_{50}$ ranging from about 0.5 µm to about 1.5 µm, for example from about 0.75 µm to about 1.25 µm.

40. The inorganic particulate material of any one of paragraphs 35 to 38, having a $d_{50}$ ranging from about 1 µm to about 2.5 µm, for example from about 1.5 µm to about 2 µm.

41. The inorganic particulate material of any one of paragraphs 35 to 40, having a $d_{98}$ equal to or less than about 8 µm, for example equal to or less than about 7 µm, for example equal to or less than about 6 µm, for example equal to or less than about 5 µm.

42. The inorganic particulate material of any one of paragraphs 35 to 41, wherein the inorganic particulate material is an alkali earth metal carbonate.

43. The inorganic particulate material of any one of paragraphs 35 to 42, wherein the inorganic particulate material is calcium carbonate, for example ground calcium carbonate (GCC).

44. The inorganic particulate material of any one of paragraphs 35 to 43, having a steepness factor ranging from about 35 to about 50, for example ranging from about 40 to about 45.

45. The inorganic particulate material of any one of paragraphs 35 to 44, wherein the inorganic particulate material is surface-treated with a hydrophobising agent.

46. The inorganic particulate material of any one of paragraphs 35 to 45, wherein the inorganic particulate material is surface-treated with an aliphatic compound.

47. The inorganic particulate material of any one of paragraphs 35 to 46, wherein the inorganic particulate material is surface-treated with a fatty acid or salt thereof, for example stearic acid or a salt thereof.

48. The inorganic particulate material of any one of paragraphs 35 to 47, wherein the coating is substantially in monolayer form.

49. The inorganic particulate material of any one of paragraphs 35 to 48, having a moisture pick-up after 48 hours equal to or less than about 0.2 wt % at 97% relative humidity, for example equal to or less than about 0.1 wt % at 97% relative humidity.
50. The inorganic particulate material of any one of paragraphs 35 to 49, wherein the % of particles smaller than 0.75 μm is equal to or less than about 40 wt %, for example equal to or less than about 37 wt %.
51. A composition comprising the inorganic particulate material of any one of paragraphs 1 to 50.
52. The composition of paragraph 51, further comprising a polymer, for example selected from polypropylene (PP), polyethylene (PE) (e.g. low density polyethylene), polyvinyl chloride (PVC), polyethylene terephthalate (PET) and any combination thereof.
53. The composition of paragraph 52, wherein the composition is a polymer film, (for example a lamination coating and/or for example a blown film, cast film or extruded film) or a synthetic paper or raffia (for example raffia tape or raffia packaging).
54. The composition of aim any one of paragraphs 51 or 53, wherein the composition comprises at least about 1 wt % of the inorganic particulate material of any one of paragraph 1 to 50, for example at least about 20 wt % of the inorganic particulate material of any one of paragraphs 1 to 50.
55. The composition of any one of paragraphs 51 to 54, wherein the composition comprises at least about 40 wt % polymer, for example at least about 50 wt % polymer.
56. The composition of any one of paragraphs 53 to 55, wherein the film has a thickness equal to or less than about 100 μm, for example equal to or less than about 50 μm, for example equal to or less than about 20 μm.
57. The composition of any one of paragraphs 53 to 56, wherein the film has a thickness ranging from 5 μm to 100 μm, for example from about 5 μm to about 20 μm.
58. The composition of any one of paragraphs 53 to 57, wherein the film is breathable, for example wherein the film has a moisture vapour transmission rate (MVTR) equal to or greater than about 2000 gsm per day, for example from about 2000 to about 15,000 gsm per day.
59. Use of the inorganic particulate material of any one of paragraphs 1 to 50 in a polymer composition (e.g. in polymeric film such as lamination coating, synthetic paper, raffia).
60. The use of paragraph 59, wherein the polymeric is selected from polypropylene (PP), polyethylene (PE) (e.g. low density polyethylene), polyvinyl chloride (PVC), polyethylene terephthalate (PET) and any combination thereof, for example wherein the polymeric film is biaxially oriented polypropylene (BOPP) or biaxially oriented polyethylene terephthalate (BOPET).
61. The use of paragraph 59 or 60, wherein the polymer composition is a polymeric film and the polymeric film is breathable.
62. A method of making a polymeric film, the method comprising:
    mixing (e.g. compounding) an inorganic particulate material of any one of paragraphs 1 to 50 with a polymer; and
    shaping the compounded material into a film.
63. The method of paragraph 62, wherein the polymer is selected from polypropylene (PP), polyethylene (PE) (e.g. low density polyethylene), polyvinyl chloride (PVC), polyethylene terephthalate (PET) and any combination thereof.
64. The method of paragraph 62 or 63, wherein the polymeric film stretched to form a breathable film.
65. Use of the inorganic particulate material of any one of paragraphs 1 to 50 as a cavitation agent.
66. Use of the inorganic particulate material of any one of paragraphs 1 to 50 in a polymeric film in order to reduce liberation of inorganic particulate material from the polymeric film and/or to reduce deposition of inorganic particulate material on the surface of the polymeric film.

EXAMPLES

Example 1

A ground calcium carbonate (GCC1) particulate material was prepared and the particle size distribution was measured by Sedigraph. The results are shown in Table 1.

TABLE 1

| Property | GCC1 |
| --- | --- |
| >25 μm (ppm) | 3.00 |
| <10 μm (wt %) | 99.60 |
| <5 μm (wt %) | 98.90 |
| <2 μm (wt %) | 84.60 |
| <1 μm (wt %) | 50.00 |
| <0.75 μm (wt %) | 35.50 |
| <0.5 μm (wt %) | 20.50 |
| $d_{50}$ (μm) | 1.00 |
| $d_{98}$ (μm) | <5 |
| Steepness Factor | ≥45 |

The GCC was surface-treated with stearic acid. Differential Scanning calorimetry (DSC) indicated a slight excess above monolayer coating. Without wishing to be bound by theory, it is though that this gives additional lubrication to the fine particles.

The surface-treated GCC1 was tested for moisture pick-up over 48 hours at a temperature of 20° C. and relative humidity of 97%. It was found that the surface-treated GCC1 had a moisture pick-up of less than 0.2 wt %.

The surface-treated GCC1 may be incorporated into a polymer without encountering processing problems such as reduced running time, despite the presence of some very coarse (larger than 25 μm) particles.

Example 2

A ground calcium carbonate (GCC2) particulate material was prepared and the particle size distribution was measured by Sedigraph. The results are shown in Table 2.

TABLE 2

| Property | GCC2 |
| --- | --- |
| >25 μm (ppm) | 5 |
| <10 μm (wt %) | 99.30 |
| <5 μm (wt %) | 94.9 |
| <2 μm (wt %) | 55.2 |
| <1 μm (wt %) | 27.0 |
| <0.75 μm (wt %) | 18.9 |
| <0.5 μm (wt %) | 11.6 |
| $d_{50}$ (μm) | 1.8 |
| $d_{98}$ (μm) | 6.2 |
| Steepness Factor | 40.1 |

The GCC2 was surface-treated with stearic acid. Differential Scanning calorimetry (DSC) indicated a slight excess above monolayer coating. Without wishing to be bound by theory, it is though that this gives additional lubrication to the fine particles.

The surface-treated GCC2 was tested for moisture pick-up over 48 hours at a temperature of 20° C. and relative humidity of 97%. It was found that the surface-treated GCC1 had a moisture pick-up of less than 0.1 wt %.

The surface-treated GCC2 may be incorporated into a polymer film without encountering processing problems such as reduced running time, despite the presence of some very coarse (larger than 25 μm) particles.

Example 3

The surface-coated GCC used in Example 1 above (GCC1) and another ground calcium carbonate surface treated with stearic acid and having an approximate particle size distribution as shown in Table 3.(GCC3) were incorporated into linear low-density polyethylene produced by a blown film line at a thickness of 30 μm. These films were then stretched on a lab machine direction orientation line between 3 and 5 times to simulate the industrial process. The films had a loading level of ground calcium carbonate between 50 and 55 wt %.

TABLE 3

| Property | GCC3 |
|---|---|
| >25 μm (ppm) | 9.00 |
| <5 μm (wt %) | 96.0 |
| <2 μm (wt %) | 58.0 |
| <1 μm (wt %) | 28.0 |
| <0.75 μm (wt %) | 20.0 |
| <0.5 μm (wt %) | 12.0 |
| $d_{50}$ (μm) | 1.7 |
| $d_{98}$ (μm) | 7.8 |

A black cloth was held against the film surfaces during stretching of the film to remove any dust. The black cloths were then viewed under a microscope at a magnification of ×25. It was surprisingly found that no particles were visible on the black cloth used with the film incorporating GCC1, whereas some particles are visible on the black cloth used with the film incorporating GCC3.

The invention claimed is:

1. An inorganic particulate material comprising:
   equal to or more than about 3 ppm of particles having a particle size equal to or greater than about 25 μm,
   equal to or less than about 40 wt % of particles smaller than about 0.75 μm,
   having a d98 less than about 11 μm, and
   wherein the % of particles smaller than 0.5 μm is equal to or less than about 25 wt %.

2. The inorganic particulate material of claim 1, comprising equal to or more than about 3 ppm of particles having a particle size equal to or greater than about 38 μm.

3. The inorganic particulate material of claim 1, having a $d_{50}$ ranging from about 0.5 to about 3 μm.

4. The inorganic particulate material of claim 1, having a $d_{98}$ equal to or less than about 8 μm.

5. The inorganic particulate material of claim 1, wherein the inorganic particulate material is ground calcium carbonate (GCC) or another alkali earth metal carbonate.

6. The inorganic particulate material of claim 1, having a steepness factor ranging from about 35 to about 50.

7. The inorganic particulate material of claim 1, wherein the inorganic particulate material is surface-treated with a hydrophobising agent.

8. The inorganic particulate material of claim 1, having a moisture pick-up after 48 hours equal to or less than about 0.2 wt % at 97% relative humidity.

9. The inorganic particulate material of claim 1, wherein the inorganic particulate material has not undergone dry sieving or sifting.

10. The inorganic particulate material of claim 1, further comprising equal to or more than about 3 ppm of particles having a particle size equal to or greater than about 40 μm.

11. A composition comprising the inorganic particulate material of claim 1, wherein the composition further comprises a polymer.

12. The composition of claim 11, wherein the composition is a film having a thickness equal to or less than about 100 μm.

13. The composition of claim 12, wherein the film has a moisture vapour transmission rate (MVTR) equal to or greater than about 2000 gsm per day.

14. A composition comprising the inorganic particulate material of claim 11, wherein the polymer is polypropylene (PP), polyethylene (PE), polyvinyl chloride (PVC), polyethylene terephthalate (PET), or a combination thereof.

15. The composition of claim 11, wherein the composition is a raffia tape, a raffia packaging, or another synthetic paper or raffia.

16. The composition of claim 11, wherein the composition is a polymer film.

17. The composition of claim 16, wherein the polymer film is a lamination coating, a blown film, a cast film or an extruded film.

18. A composition comprising the inorganic particulate material of claim 1, wherein the composition is a cavitation agent.

19. A method of making a polymeric film, the method comprising:
   forming a compounded material by mixing an inorganic particulate material of claim 1 with a polymer; and
   shaping the compounded material into a film.

* * * * *